United States Patent
Vogel

(10) Patent No.: US 12,178,665 B2
(45) Date of Patent: Dec. 31, 2024

(54) MARKING BODY, METHOD FOR THE PRODUCTION AND USE OF A MARKING BODY

(71) Applicant: ALLEIMA KARLSRUHE GMBH, Karlsruhe (DE)

(72) Inventor: Bernd Vogel, Karlsruhe (DE)

(73) Assignee: Alleima Karlsruhe GmbH, Karlsruhe (DE)

( * ) Notice: Subject to any disclaimer, the term of this patent is extended or adjusted under 35 U.S.C. 154(b) by 876 days.

(21) Appl. No.: 16/540,931

(22) Filed: Aug. 14, 2019

(65) Prior Publication Data
US 2020/0054413 A1    Feb. 20, 2020

(30) Foreign Application Priority Data
Aug. 14, 2018    (EP) .................................... 18000672

(51) Int. Cl.
*A61B 90/00*    (2016.01)
*A61B 17/00*    (2006.01)

(52) U.S. Cl.
CPC .... *A61B 90/39* (2016.02); *A61B 2017/00526* (2013.01); *A61B 2017/00867* (2013.01); *A61B 2017/00942* (2013.01); *A61B 2090/3908* (2016.02); *A61B 2090/3925* (2016.02); *A61B 2090/3966* (2016.02); *A61B 2090/3991* (2016.02)

(58) Field of Classification Search
CPC ........... A61B 2017/00867; A61B 2017/00942; A61B 90/39; A61B 2090/3991; A61F 2/02; A61F 2/0108
See application file for complete search history.

(56) References Cited

U.S. PATENT DOCUMENTS

| | | | | |
|---|---|---|---|---|
| 2002/0002401 A1* | 1/2002 | McGuckin, Jr. | ...... | A61F 2/2475 623/1.36 |
| 2004/0220610 A1* | 11/2004 | Kreidler | .................. | B32B 27/08 606/151 |
| 2005/0015111 A1* | 1/2005 | McGuckin, Jr. | ........ | A61F 2/012 606/200 |
| 2007/0093726 A1* | 4/2007 | Leopold | ................. | A61B 90/39 600/562 |
| 2014/0371778 A1* | 12/2014 | Rudakov | .......... | A61B 17/12036 606/198 |
| 2019/0076212 A1* | 3/2019 | Liu | ........................ | A61B 90/39 |
| 2019/0201160 A1* | 7/2019 | Hornscheidt | .......... | A61B 90/39 |

FOREIGN PATENT DOCUMENTS

DE    102016110350 A1    12/2017

* cited by examiner

*Primary Examiner* — Sarah A Long
*Assistant Examiner* — Raihan R Khandker
(74) *Attorney, Agent, or Firm* — Morgan, Lewis & Bockius LLP

(57) ABSTRACT

A marking body, a method for producing a marking body and a method for using a marking body are disclosed. In an embodiment a marking body includes a self-expanding structure of a shape-memory metal, wherein the shape-memory metal forms a tubular structure that has at least two elongated openings along its length that extend no further than from a head section to a foot section of the tubular structure, wherein the tubular structure comprises at least one stripe of the shape-memory metal located between two adjacent elongated openings, and wherein the tubular structure is configured to be compressed when in an application condition and configured to be stretched when in a non-application condition.

26 Claims, 5 Drawing Sheets

MARKING BODY, METHOD FOR THE PRODUCTION AND USE OF A MARKING BODY

CROSS-REFERENCE TO RELATED APPLICATIONS

This application claims priority to European Patent Application No. 18 000 672.8, filed on Aug. 14, 2018, which application is hereby incorporated herein by reference.

TECHNICAL FIELD

The invention refers to a marking body, formed for marking tumor cells in tissue.

BACKGROUND

On the state of the art, marking bodies are known that are introduced into tumour-cell-containing areas in tissues in order to mark the tumor cells. The marking bodies usually are at least partially made of metal, due to which they stand out from surrounding body cells in examination with imaging methods and therefore can be detected easily. This way, they facilitate the finding of affected tissue areas at different stages of treatment, which is necessary for targeted treatment of affected regions and for review of success.

Marking bodies of a polymer core surrounded by a steel jacket or pure titanium or stainless-steel bodies transported to the location to be marked with a cannula and released there are common. However, their small diameters reduce their visibility in imaging methods. They also often do not stay in the intended location and therefore have a low reliability. Other marking bodies are made of a shape memory share wound into a spiral that will take on a ring form after placement in the tissue. They are better visible when looking at the ring circumference, but not from the sides. Therefore, placement of such a marking body requires the greatest diligence and expertise of the medical staff.

DE 10 2016 110 350 A1 describes a marking body for implantation in a tissue with a compressible and self-expanding carrying structure formed by at least one elastic metal wire that encloses an inner space in an expanded condition, wherein the marking body is formed to change independently from a compressed condition into an expanded condition, also against a tissue pressure present at a tissue point to be marked, with the marking body having a hollow, near-spherical shape in the expanded condition. Due to its structure formed of wires, such a marking body has a low radial force in expansion, which may be problematic for firmer tissue types.

SUMMARY

Embodiments provide an improved marking body.

Further embodiments provide a method for producing an improved marking body in a simplified production process Yet further embodiments provide a method for using the marking body.

SUMMARY

A marking body according to embodiments of the invention that is formed for marking of tumor cells in tissue has a self-expanding structure of a shape memory metal in a first embodiment, wherein the shape-memory metal forms a tubular structure. It has at least two elongated openings along its length that do not expand any further than from a head section to a foot section of the tubular structure. In an application condition, the tubular structure is present compressed and strips of shape-memory metal remaining between two elongated openings adjacent to each other each protrude. In a non-application condition, the tubular structure is present stretched.

In this case, self-expanding means that the shape-memory metal transitions into a shape of larger volume without the influence of any outer forces. The marking body according to embodiments of the invention, which is not made of wire, is beneficially suitable to apply a high expansion pressure.

Here, the application condition is a condition of the marking body when it is not exposed to any forces deforming it, i.e. if the structure itself is expanded. Generally, the application condition may be a condition the marking body takes when it has, e.g., reached its final position in a location to be marked, e.g. a tissue, in order to remain there. In contrast to this, the non-application condition is the condition in which the marking body is deformed under the influence of outer forces. This may be a transport condition during which the marking body is already ready for application in the cannula, or another condition in which the marking body is prepared but not yet ready for application.

The tubular structure is deemed compressed here when it is compressed lengthwise, and therefore shortened, and stretched when this shortening under the influence of outer forces has been reversed.

This embodiment is beneficial because a shape-memory metal can be used to produce a marking body that protrudes voluminously in the application condition. The protrusion of the strips expands the circumference of the marking body, which beneficially increases its visibility and therefore traceability in imaging methods, in particular in X-ray and ultrasound examinations. Since ultrasound examinations put far less of a strain on the human body than X-ray methods, increased visibility in these is particularly beneficial.

When transitioning into the application condition, the marking body according to embodiments of the invention applies a higher radial force onto its environment through its protruding strips than known marking bodies do, which allows the self-expanding structure of shape-memory metal to expand completely even in environments with a higher firmness.

Use of the shape-memory metal permits definition of the structure desired for the application condition during production. For transport and during implantation into tissue, for example, the tubular structure is present in the stretched shape, which beneficially means a lower space requirement and a better, lower-friction transport through a cannula needed for introduction into tissue.

In another embodiment of the marking body, the head section of the tubular structure is a head collar and the foot section is a foot collar. In this context, head or foot collar means that cohesion of the strips is present at least at these collars. This way, the marking body takes on nearly ellipsoid structures in the application condition. The elongated openings in the marking body can run in parallel with each other at least for a portion or entirely; they can be cuts and/or recesses running between the head section and the foot section axially or helically.

In accordance with another embodiment of the marking body, the shape-memory metal of the marking body is nitinol. Here, nitinol means a nickel-titanium alloy wherein the name is an acronym for "Nickel Titanium Naval Ordnance Laboratory". With its super-elastic properties, it is suitable for use in medical-technology products and can be processed with known processing methods. Since nitinol has biomechanical properties similar to those of human tissue, it can withstand the stresses it is exposed to in the application condition. Nitinol also beneficially is a biocompatible material that does not cause any defense reactions in contact with body cells.

The tubular shape memory structure can be a sheet bent into a tube that is closed on the longitudinal side or that still has an opening slit on the longitudinal side, or a tube. The production from a single sheet, tube or tube portion leads to a cost-efficient production as well as to a shape that can be handled particularly well, since the smooth outer contour makes the marking body easy to clean and very easy to handle in a cannula.

Opening types of the axial and helical openings running between the head section and the foot section can be combined as well.

Helically means that the cuts or recesses wind around the jacket surface of the tubular structure, wherein the number of the surrounding circumferences is arbitrary and may be less than one. The number of cuts and recesses and their distance from each other at the same time specifies the strip number and width. Cuts are the easiest and therefore most cost-efficient version for the elongated openings. Recesses with material removal or a combination of cuts and recesses may produce a plurality of different designs. These may beneficially mark different body regions in designs that are distinguishably recognisable in imaging methods.

In another embodiment of the marking body, it comprises anchoring means. Beneficially, at least one strip has at least one anchoring means along the circumferential direction and/or along its length. The anchoring means is preferably formed by a tab that is provided by one or several cut(s) or recess(es) that is/are introduced into the strip. In this, the tab has a root through which it is radially movably connected to the strip. The root of each of the tabs is connected to one of the head or foot sections or is preferably offset against it.

In this, movable means that the tab is moved at the transition from the non-application condition to the application condition. Specifically, the exposed tab can bend open further in the radial direction from its head end beyond the protrusion of the individual strips and curve in the scope of this. The tab thus points into the surrounding tissue with its head end in the application condition and beneficially forms an anchoring means that, comparable with a hook, can fixate the marking body in the environment in its position, which is otherwise only done via the press-on pressure of the marking body to its environment. It is also beneficial in this embodiment that the anchoring means can also be produced of the tubular structure, by which the smooth outer contour of the marking body is preserved.

If several strips have tabs, it is beneficially possible to arrange the tabs, e.g., rotation-symmetrically, so that the marking body can anchor in the surrounding tissue in several directions, which increases reliability of the anchor. Apart from this, this simplifies provision of the marking body in the cannula, since it does not need to be present or introduced into the tissue in a specified rotational alignment. A preferred embodiment has one tab at each strip.

If the roots of the tabs are applied offset against the head section or foot section in the longitudinal direction, the tabs are shorted and therefore more stable, and the strips with tabs also are more stable in the area of the tab root than in roots that are not offset.

An attachment of several tabs at a strip beneficially increases flexibility of the design of the anchoring and various recognisable designs.

According to a further embodiment, at least one tab can have several ends, preferably tips or rounded tips, at its head end. Preferably, the cut or cuts are U-shaped or W-shaped. Rounded tips form tissue-preserving anchoring points. Tabs with one tip or rounded tip, as they are produced by V- or preferably U-shaped cuts, are sufficient and beneficial for simple anchoring, since they can be produced very simply. W-shaped cuts produce tabs with two tips. This increases the probability that at least one tip anchors in the manner intended. Depending on embodiment, the material in between can be removed or remain connected to the tube and form a tab in turn that can be moved in the opposite direction. Such a combination of opposing tabs can beneficially increase reliability of the anchoring. Further cut shapes that produce one, two or more ends, e.g. non-closed, trapezoidal cuts, are imaginable.

Furthermore, it can be intended that the head section or the foot section of the tubular structure, or both, is or are applied with a closure element. The closure element is preferably a cap and beneficially increases visibility of the marking body in imaging methods when the line of sight is axial to the tubular structure.

In accordance with another embodiment of the marking body, an elongated body is arranged in the tubular structure, preferably a pin or tube, which has a material chosen from the group comprising ferromagnetic metals and alloys, shape-memory metals and polymers, preferably conductive polymers, or combinations of the above. Such a body increases visibility in the axial viewing direction as well. Apart from this, it can be beneficially formed as a doped polymer that has a characteristic appearance in an imaging method and therefore permits distinguishability of different marking bodies applied in different locations. If the inserted body is magnetic, it beneficially offers the additional option of detecting the placed marking body via magnetic field analysis.

It can further be intended that the marking body has a housing of a hydrophilic, swelling substance, preferably of a hydrogel or a collagen, wherein the self-expanding structure of the shape-memory metal is present in the compressed condition in the housing.

The housing here is to be understood as a filled housing that virtually forms a bed with a defined outer contour for the compressed, enclosed marking body. In this, the inner space of the marking body may be wholly or partially filled. Such a housing, which is initially present in a dry condition, will swell and enlarge its volume to a multiple when coming into contact with a water-containing medium, which may be, e.g., a tissue fluid, upon insertion of the marking body. This beneficially supports expansion of the marking body. In design of the marking body in a preferred embodiment of nitinol, the body may expand particularly strongly due to its super-elastic material properties and the volume expansion therefore may be transferred to the marking body particularly beneficially.

In another embodiment, the tubular structure has a diameter in the range of 2 mm to 15 mm in its farthest protruding point in the application condition, preferably in the range of 3 mm to 8 mm, and a length in the range of 2 mm to 15 mm, preferably in the range of 4 mm to 9 mm. These dimensions beneficially mean that the marking body is sufficiently small in the non-application condition to be provided in a cannula and inserted into tissue by minimally invasive surgery, and sufficiently large in the application condition to ensure high traceability of the marked location when applying imaging methods.

In embodiments a method for producing a marking body comprises the following steps:
a) provision of a semi-finished product in the form of a tube or sheet of a shape-memory metal,
b) introduction of the at least two elongated openings along the longitudinal side of the semi-finished product between the head section and foot section, and, if the semi-finished product is present in the form of a sheet,
b') bending of the sheet along its longitudinal axis until it reaches a tubular structure,
c) grasping the head section and foot section with a tool and applying an axial force while compressing the semi-finished product,
d) heating the semi-finished product to a target temperature and holding the target temperature for a target duration, while imprinting the shape of the semi-finished product during compression on the semi-finished product,
e) letting the semi-finished product cool off.

The semi-finished product can, therefore, be a tube or a sheet bent into a tubular structure of nitinol or another shape-memory metal. The production therefore assumes a single workpiece and, therefore, can be performed easily and cost-efficiently.

The openings can, for example, be introduced into the semi-finished product by laser-cutting, a method particularly preferred and suitable for nitinol. However, other processing methods suitable for the respective shape-memory metal used are also possible, e.g. (non-comprehensive list) waterjet cutting or wire erosion.

The target temperature to activate the shape memory usually is in the range of 400 to 650 degrees Celsius and is preferably held for a target duration of no more than three minutes, particularly preferably for no more than one minute. Shorter holding durations are known to accelerated production and are therefore cost saving.

Heating may take place externally, e.g. by heating via the tool, or internally, e.g. by inductive heating or application of an electrical voltage to the head and foot sections of the semi-finished product that heats up due to a resistance opposing an electrical current.

The method for production of a marking body of a tube or sheet can additionally include the production of at least one anchoring means after step b) by introduction of cuts or recesses in at least one of the strips, and
bending open of the anchoring means in the radial direction, no further than to the root, as step c').

With this method, marking bodies according to embodiments of the invention can be produced that have anchoring means, in particular tabs, for anchoring of the marking body in the place to be marked. The anchoring means are brought to the application position before the step of heating d) so that this shape is imprinted.

Use of a marking body according to embodiments of the invention intends for use as a marker for tumor cells in a tissue. For this, the marking body is produced and provided in a cannula in the non-application condition. Using an imaging method, a location of the human body that is affected by tumor cells is then determined and the cannula is placed so that the marking body can be pushed through the cannula and will leave the cannula in the intended location. When leaving the cannula, the marking body according to embodiments of the invention will transition into the application condition by way of expansion of the self-expanding structure of shape-memory metal. The volume expansion makes the marking body apply a press-on pressure to the tissue surrounding it and thereby adheres there. If the marking body has anchoring means, these will transition into a bent-open position as well at the transition to the application condition, so that they can additionally anchor the marking body. Thus, the body location in which the marking body is placed is marked so that it can be found again using an imaging method, in particular ultrasound, since the marking body is particularly well visible in such imaging methods. This visibility is retained even if the tumor cells as such are no longer present or no longer present at the same amount as before due to the applied treatment method, and the marked location therefore cannot be clearly determined anymore by localisation of tumor cells.

BRIEF DESCRIPTION OF THE DRAWINGS

Further embodiments and some of the benefits connected to these and further embodiments become clear and better comprehensible by the following detailed description with reference to the accompanying figures. Objects or parts of these that are essentially the same or similar may be applied with the same reference signs. The figures are only a schematic illustration of an embodiment of the invention.

FIG. 2b shows a longitudinal view of the marking body of FIG. 2a;
FIG. 2c shows a frontal view of the marking body of FIG. 2a.

DETAILED DESCRIPTION OF ILLUSTRATIVE EMBODIMENTS

The device according to embodiments of the invention refers to a marking body, formed for marking of tumor cells in tissue, as shown in FIG. 1 to 6b.

Figure 1:
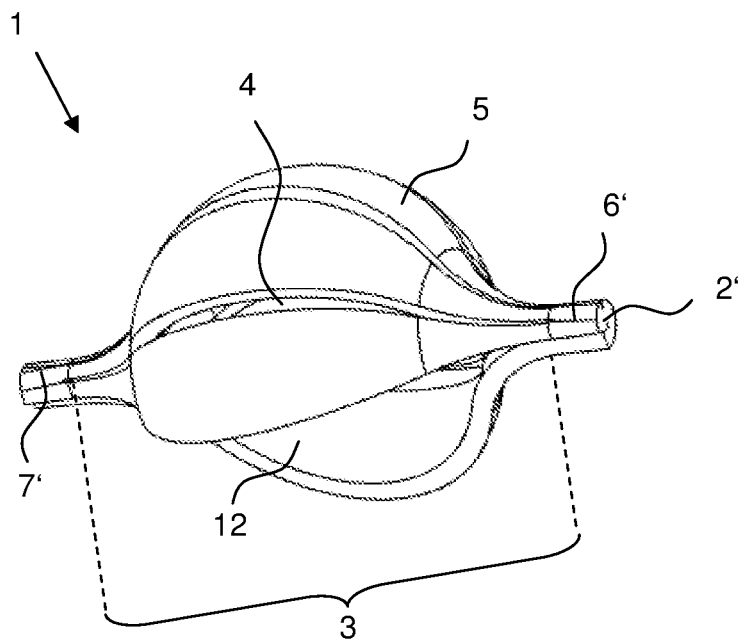
FIG. 1 shows a perspective view of a marking body of a sheet.

FIG. 1 shows a marking body 1 according to an embodiment of the invention in the application condition. It therefore has the shape memory structure 3 that it also has when it is, e.g., inserted in a tissue. It comprises of a sheet 2' of a shape-memory metal bent into a tube that still has an opening slit 12 on the long side. It also has six elongated openings 4 that are, in this case, cuts that run between the head collar 6' and the foot collar 7', and thus also six strips 5 that run between these. These form the protruded shape memory structure 3 illustrated here that offers an enlarged volume and a high visibility in different viewing directions when viewing via an imaging method due to the broad strips 5. A radial force acts on the environment of the marking body 1 that adheres there in this manner via the strips 5. The figures do not show the associated non-application condition of the marking body 1, which is then present stretched, and therefore not protruding, and that can be easily pre-loaded in a cannula and moved in it due to its tubular structure.

Generally, it can be said that the number of elongated openings 4 in all marking bodies 1 can be rather at least at 3, 4, 5, 6 or potentially even higher, at up to 14, in order to achieve an ideally spherical shape of the area placed between the head and foot sections 5, 6. There only must not be as many openings or cuts that the structure becomes unstable or even wire-like.

Figure 2A:
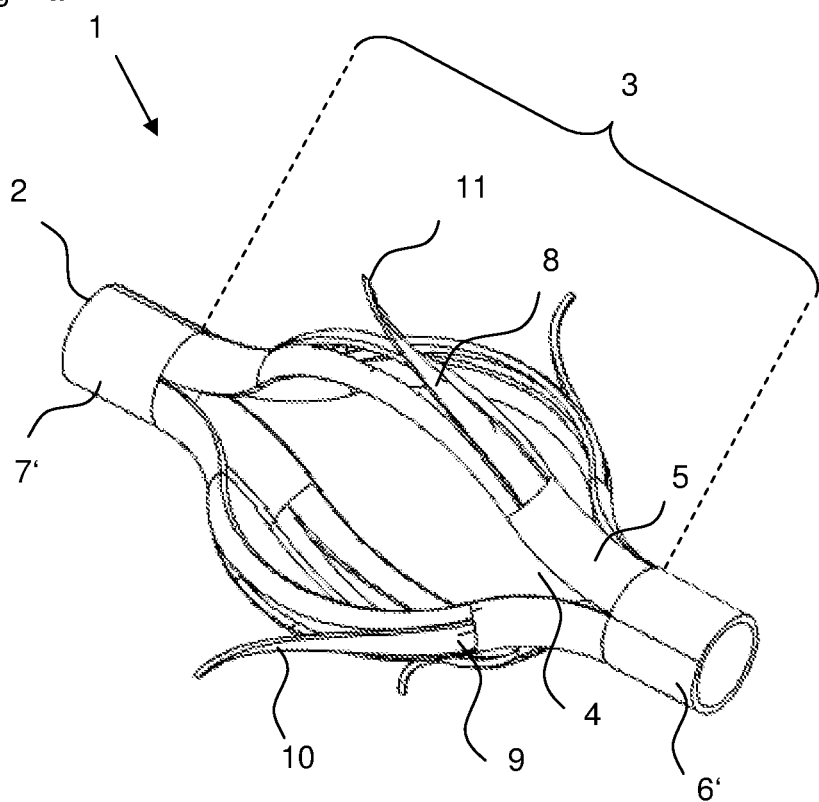
FIG. 2a shows a perspective view of a marking body with anchoring means.
Figure 2B:
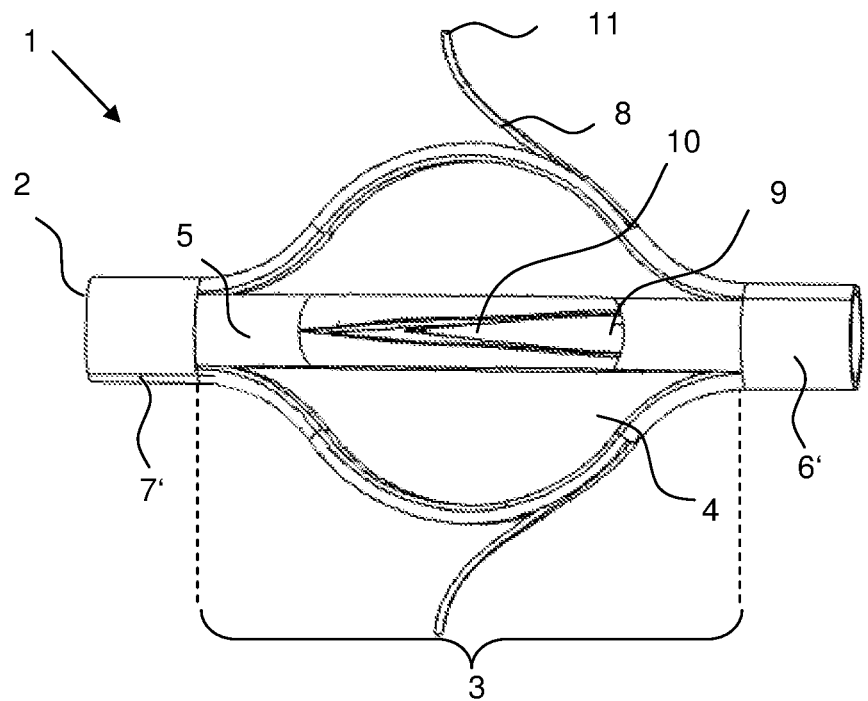
Figure 2C:
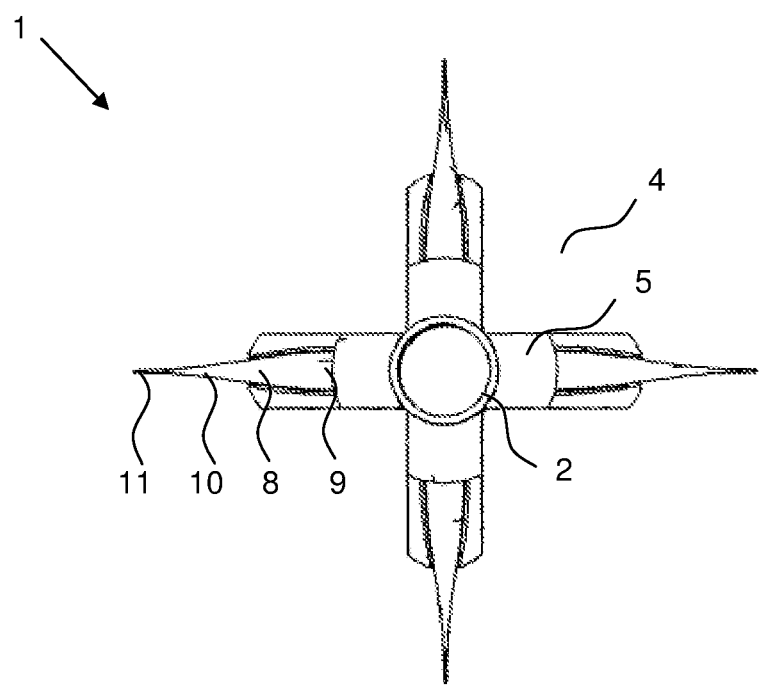

FIG. 2a to 2c show a marking body 1 with anchoring means in the application condition, wherein the anchoring means here are tabs 8. The marking body here is made of a tube 2 of a shape-memory metal. It has four elongated openings 4 that are present here in the form of four parallel cuts along the length of the tube 2. The four strips 5 formed in this manner run between the head collar 6' and the foot collar 7' (not visible in in FIG. 2c), since the cuts start or end there. In the application condition shown in FIG. 2a to 2c, the strips protrude between the head 6' and foot collar 7' and thus form the framework of the shape memory structure.

In the illustrated embodiment, each strip 5 is cut in V-shaped, wherein the V-shaped cuts touch neither the head collar 6', nor the foot collar 7', nor the openings 4 between the strips 5. Thus, a tab 8 is exposed in each strip 5 as anchoring means. Each tab 8 has a tip 11 at its head end 10. The tips point away from the shape memory structure 3 into the environment, as is visible particularly well in FIGS. 2b and 2c. If the marking body 1 is, for example, placed in a tissue area affected by tumor cells, it can be additionally fixated in the surrounding tissue in four locations via these tips. The tabs 8 are connected to the strip 5 into which they are cut via their roots 9. The roots 9 are offset towards the foot collar 7', facing the head collar 6'.

Figure 3:
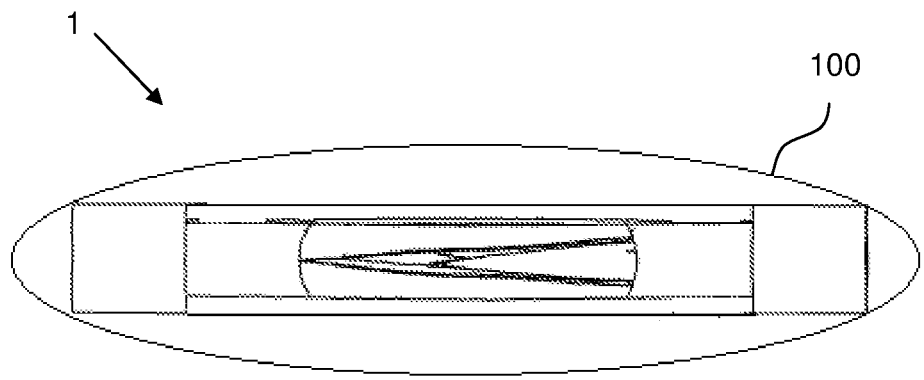
FIG. 3 shows a marking body in accordance with FIG. 2a, b, c with housing.

FIG. 3 shows a marking body 1 with housing 100 in the non-application condition and therefore shaped tubular. The material that forms the housing is, for example, a hydrogel and present in a dry condition in and around the marking body. In this condition, the marking body can be brought to the location to be marked. It is not illustrated that the hydrogel will swell when in contact with liquid, which supports unfolding of the shape memory structure and that the entire marking body thereby clearly expands its volume.

Figure 4A:
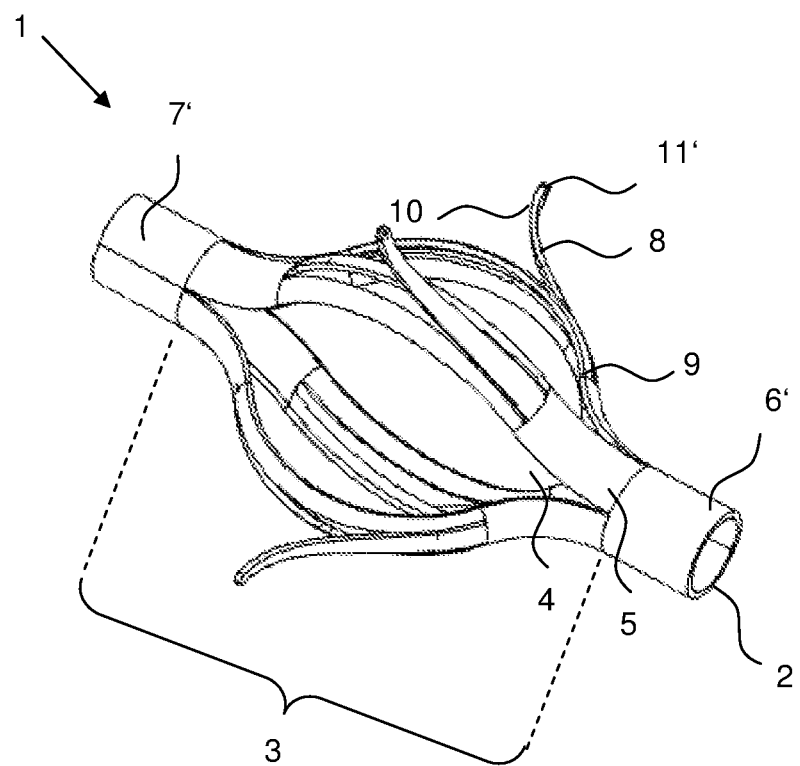
FIG. 4a shows a marking body with anchoring means with rounded tips.

FIG. 4a shows a marking body 1 built similarly to the marking body 1 in FIG. 2. It has four elongated openings 4 and four strips 5, wherein in each strip 5 has a tab 8 inserted in it. In contrast to the marking body in FIG. 4, however, the tabs in this embodiment are produced by U-shaped cuts so that the tips 11' of the tabs 8 are rounded, which becomes particularly clear by direct comparison of FIG. 2a and FIG. 4a.

Figure 4B:
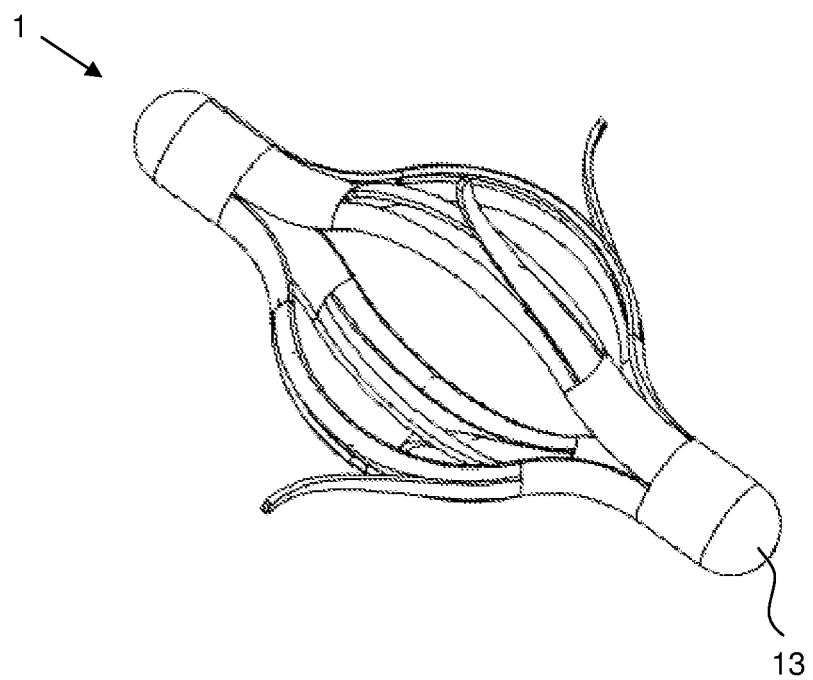
FIG. 4b shows the marking body of FIG. 4a with caps.
Figure 4C:
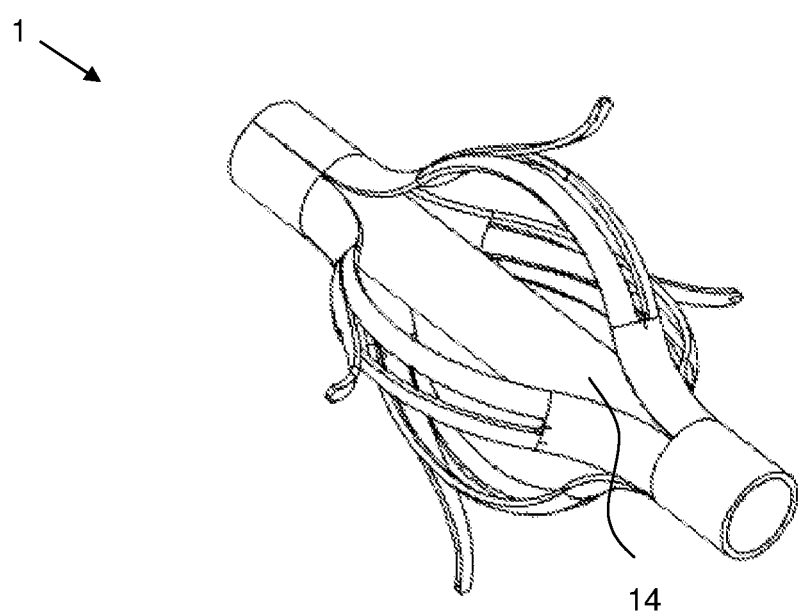
FIG. 4c shows the marking body of FIG. 4a with inserted pin.

The marking body 1 shown in FIG. 4b corresponds to that of FIG. 4a, but has caps 13 as an additional feature that are attached to the head collar 6' and foot collar 7' as closure elements. The marking body 1 of FIG. 4a, which has a pin on the inside, is shown in FIG. 4c. Both are embodiment variations that increase visibility of the marking body 1 and form design variations for the image of the marking body 1 visible in the imaging method.

Figure 5:
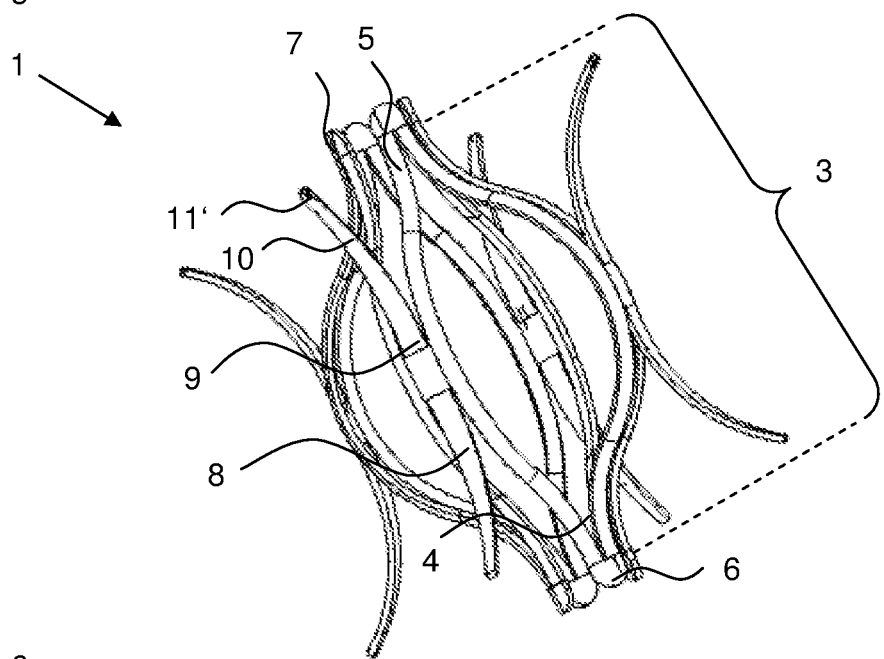
FIG. 5 shows a marking body with partially opened head and foot section.

FIG. 5 shows a marking body that has further recesses and cuts in addition to the four axial cuts 4. Above and below the openings 4, a head section 6 and foot section 7 each are left standing. Recesses run inside of head section 6 and foot section 7 as well in this. Four strips 5 have two U-shaped cuts placed in them each, forming anchoring means. One pair of opposing tabs 8 that face away from each other with their rounded tips 11' is placed on each strip 5. The symmetrical arrangement of the tabs prevents the marking body 1 from moving away in various directions.

Figure 6A:
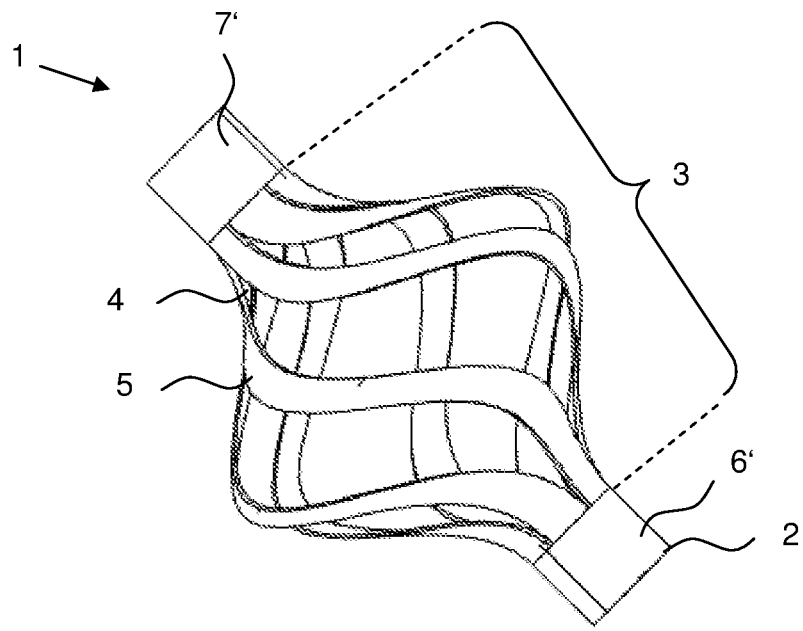
FIG. 6a shows a marking body with helical cuts.
Figure 6B:
FIG. 6b shows the marking body of FIG. 6a in the non-application condition.

FIGS. 6a and 6b show a marking body 1 made of a tube 2 into which six cuts 4 are introduced that run helically between the head collar 6' and foot collar 7', winding a little more than once around the circumference of the tube 2, but no further cuts or recesses. FIG. 6b shows the marking body in the non-application condition. The tubular structure, which can be transported through a cannula particularly easily and with low friction, becomes clear here. In the application condition of this marking body 1, which is visible in FIG. 6a, the shape memory structure 3 formed by the six protruded strips 6 has expanded. The figures are only schematic illustrations, and in particular the size ratios between the application and the non-application condition are not reflected in the figures.

REFERENCE CHARACTER LIST

1 Marking Body
2, 2' Tube, sheet
3 Shape memory structure
4 Elongated opening
5 Strip
6, 6' Head section, head collar
7, 7' Foot section, foot collar
8 Tab
9 Root
10 Head area
11, 11' Tip, rounded tip
12 Opening slit
13 Cap
14 Pin
100 Housing

What is claimed is:
1. A marking body, comprising:
a self-expanding structure of a shape-memory metal,
wherein the shape-memory metal is a tubular structure extending axially between a first end and a second end and having at least two elongated openings along a long side extending from a head section to a foot section of the tubular structure,
wherein the head section includes a first circumferentially continuous surface that extends axially inward from the first end of the tubular structure to an inward head edge and the foot section includes a second circumferentially continuous surface that extends axially inward from the second end of the tubular structure to an inward foot edge,
wherein the shape-memory metal located circumferentially between the at least two elongated openings defines a strip in the shape-memory metal,
wherein, when the tubular structure is compressed in a first configuration, the strip of the shape-memory metal bulges between two adjacent elongated openings,
wherein, when the tubular structure is stretched in a second configuration, the tubular structure has a tube shape and the strip of the shape-memory metal forms part of a wall of the tube shape of the tubular structure,
wherein the strip comprises two anchors along a length direction,
wherein each of the two anchors is formed by one or more cuts or recesses in the strip, and is an elongate curved structure including a first end and a second end,
wherein the first end of each of the two anchors is connected to an intermediate section of the strip via a root and the second end of each of the two anchors is independently radially movable relative to the strip, wherein the intermediate section is offset in a longitudinal direction from the head section and the foot section, wherein the second end of a first of the two anchors extends in the longitudinal direction toward the head section and the second end of a second of the two anchors extends in the longitudinal direction toward the foot section, and wherein, when in the second configuration, the second end of the first of the two anchors extends to the inward head edge and the second end of the second of the two anchors extends to the inward foot edge.

2. The marking body according to claim 1, wherein the head section is a head collar and the foot section is a foot collar.

3. The marking body according to claim 1, wherein the at least two elongated openings run at least partially in parallel to each other.

4. The marking body according to claim 1, wherein the at least two elongated openings run axially or helically between the head section and the foot section.

5. The marking body according to claim 1, wherein the shape-memory metal is nitinol.

6. The marking body according to claim 1, wherein the shape-memory metal is a sheet bent into the tubular structure.

7. The marking body according to claim 1, wherein each anchor comprises an U-shape or a W-shape.

8. The marking body according to claim 1, wherein the second end of each anchor comprises a pointed tip or a rounded tip.

9. The marking body according to claim 1, further comprising a closure element at the head section and/or foot section of the tubular structure.

10. The marking body according to claim 9, wherein the closure element is a cap.

11. The marking body according to claim 1, further comprising a pin or a tube arranged in the tubular structure.

12. The marking body according to claim 11, wherein the pin or the tube comprises a ferromagnetic metal, a ferromagnetic alloy, a shape-memory metal or polymer, a conductive polymer, or combinations thereof.

13. The marking body according to claim 1, wherein the marking body comprises a housing when in the second configuration.

14. The marking body according to claim 13, wherein the housing comprises a hydrophilic, swelling substance.

15. The marking body according to claim 14, wherein the swelling substance is a hydrogel or a collagen.

16. The marking body according to claim 1, wherein the tubular structure has a diameter in a range of between 2 mm to 15 mm, inclusive, in its widest extension when in the first configuration, and a length in the range of between 2 mm to 15 mm, inclusive.

17. The marking body according to claim 1, wherein the at least two elongated openings are elongated openings between 3 and 14, inclusive.

18. The marking body according to claim 1, wherein the at least two elongated openings are exactly four elongated openings or exactly six elongated openings.

19. A marking body, comprising:

a self-expanding structure of a shape-memory metal, wherein the shape-memory metal is a tubular structure having at least two elongated openings along a long side extending no further than from a head section to a foot section of the tubular structure, wherein the at least two elongated openings form at least one strip in the shape-memory metal, wherein, when the tubular structure is compressed in a first configuration, the at least one strip of the shape-memory metal bulges between two adjacent elongated openings, wherein, when the tubular structure is stretched in a second configuration, the at least one strip of the shape-memory metal forms part of a tube shape of the tubular structure, wherein the at least one strip comprises at least two anchors along a length direction, wherein each of the at least two anchors is formed by one or more cuts or recesses in a respective strip, wherein a first end of each of the at least two anchors is connected to the respective strip via a root in a middle of the respective strip, wherein a second end of a first of the at least two anchors extends in a first direction, a second end of a second of the at least two anchors extends in a second direction, and the first direction is opposite to the second direction, wherein, when in the first configuration, both the first of the at least two anchors and the second of the at least two anchors have a curved shape, and wherein, when in the second configuration, the second end of the first of the at least two anchors extends to an axially inward edge of the head section and the second end of the second of the at least two anchors extends to an axially inward edge of the foot section.

20. The marking body according to claim 19, wherein the first direction is toward the head section of the tubular structure and the second direction is toward the foot section of the tubular structure.

21. A marking body, comprising:

a self-expanding structure of a shape-memory metal, wherein the shape-memory metal is a tubular structure having at least two elongated openings along a long side extending no further than from a head section to a foot section of the tubular structure, wherein the at least two elongated openings form at least one strip in the shape-memory metal, wherein, when the tubular structure is compressed in a first configuration, the at least one strip of the shape-memory metal bulges between two adjacent elongated openings, wherein, when the tubular structure is stretched in a second configuration, the at least one strip of the shape-memory metal forms part of a tube shape of the tubular structure, wherein the at least one strip comprises a length, a width and a height, the length being larger than the width and the width being larger than the height, wherein at least two anchors are cut out from or recessed within a surface of the at least one strip, the surface being defined by the length and the width, wherein each of the at least two anchors are connected to the respective strip via a root, and are radially movable relative to the respective strip, wherein the root of each of the at least two anchors connects a first end of each of the at least two anchors to an intermediate section of the respective strip that is offset in a longitudinal direction from the head section and the foot section, wherein a first of the at least two anchors extends in the longitudinal direction toward the head section and a second of the at least two anchors extends in the longitudinal direction toward the foot section, wherein, when in the first configuration, each of the first of the at least two anchors and the second of the at least two anchors has a curved shape that extends from the root to a tip of the respective anchor, and wherein, when in the second configuration, the second end of the first of the at least two anchors extends to an axially inward edge of the head section and the second end of the second of the at least two anchors extends to an axially inward edge of the foot section.

22. A marking body, comprising:
a self-expanding structure of a shape-memory metal,
wherein the shape-memory metal is a tubular structure having at least two elongated openings along a long side extending no further than from a head section to a foot section of the tubular structure,
wherein the at least two elongated openings form at least one strip in the shape-memory metal,
wherein, when the tubular structure is compressed in a first configuration, the at least one strip of the shape-memory metal bulges between two adjacent elongated openings,
wherein, when the tubular structure is stretched in a second configuration, the at least one strip of the shape-memory metal forms part of a tube shape of the tubular structure,
wherein the at least one strip comprises at least two anchors along a length direction,
wherein each of the at least two anchors is formed by one or more cuts or recesses in a respective strip,
wherein each of the at least two anchors has a root and a head end, is connected directly to the respective strip via the root, and the head end is radially movable relative to the respective strip,
wherein, when in the first configuration, a first of the at least two anchors extends in the length direction in a first curve toward the head section and a second of the at least two anchors extends in the length direction in a second curve toward the foot section,
wherein the head end is bent further in a radial direction beyond a bulge of the respective strip when in the first configuration so that the head end of each of the at least two anchors points towards a surrounding structure thereby making the marking body fixable to the surrounding structure, and
wherein, when in the second configuration, the second end of the first of the at least two anchors extends to an axially inward edge of the head section and the second end of the second of the at least two anchors extends to an axially inward edge of the foot section.

23. A marking body, comprising:
a self-expanding structure of a shape-memory metal,
wherein the self-expanding structure is a tubular structure having a plurality of elongated openings along a long side extending no further than from a head section to a foot section of the tubular structure,
wherein the plurality of elongated openings form at least one strip in the shape-memory metal,
wherein the at least one strip includes a body portion and two anchor portions, wherein the body portion extends between the head section and the foot section of the tubular structure,
wherein each of the two anchor portions is elongate and extends in a length direction and has a first end connected to the body portion of the respective strip via a root,
wherein the root is located in the respective strip spaced apart from the head section and the foot section,
wherein each of the two anchor portions has a second end that is non-connected to the body portion of the respective strip,
wherein the second end of a first of the two anchor portions extends in the length direction toward the head section and the second end of a second of the two anchor portions extends in the length direction toward the foot section,
wherein, in a non-extended position, the second end of the first of the two anchor portions extends to a position proximate the head section and the second end of the second of the two anchor portions extends to a position proximate the foot section, and
wherein, in an extended position, each of the two anchor portions extends outwardly in a curve in the length direction.

24. The marking body according to claim 23, wherein the second end of each of the two anchor portions is radially movable relative to the body portion of the respective strip, and
wherein, in the extended position, the second end of each of the two anchor portions is radially outward relative to the body portion of the respective strip.

25. A marking body, comprising:
a self-expanding structure of a shape-memory metal,
wherein the self-expanding structure is a tubular structure including a long side wall and a plurality of elongated openings in the long side wall that extend no further than from a head section to a foot section of the tubular structure,
wherein the plurality of elongated openings form at least one strip in the shape-memory metal,
wherein the at least one strip comprises a body having a length, a width and a height, the length being larger than the width and the width being larger than the height,
wherein at least two anchors are cut out from or recessed within a surface of the body of the at least one strip, the surface being defined by the length and the width,
wherein a first end of each of the at least two anchors is connected to the respective strip via a root and a second end of each of the at least two anchors is radially movable relative to the body of the respective strip,
wherein, in each of the at least two anchors, the root connects the first end of the respective anchor to the body of the respective strip at a position spaced apart from the head section of the tubular structure and the foot section of the tubular structure,
wherein the tubular structure has a first configuration when compressed and a second configuration when stretched,
wherein, in the first configuration, the body of the at least one strip bulges radially outward between two adjacent elongated openings and each of the at least two anchors has a curved shape extending between the first end and the second end, and
wherein, in the second configuration, the second end of a first of the at least two anchors extends in a first direction toward the head section to a position proximate the head section of the tubular structure and the second end of a second of the at least two anchors extends in a second direction toward the foot section to a position proximate the foot section of the tubular structure.

26. The marking body according to claim 25, wherein, in the second configuration, the body of the at least one strip is contained within the long side wall of the tubular structure.

\* \* \* \* \*